(12) United States Patent  (10) Patent No.: US 8,009,294 B2
Shpantzer et al.  (45) Date of Patent: *Aug. 30, 2011

(54) CHEMICAL SENSING SYSTEM AND METHOD

(75) Inventors: Isaac Shpantzer, Bethesda, MD (US); Jacob Khurgin, Baltimore, MD (US); Arkady Kaplan, Rockville, MD (US); Pak Shing Cho, Gaithersburg, MD (US); Yaakov Achiam, Rockville, MD (US)

(73) Assignee: CeLight, Inc., Silver Spring, MD (US)

(*) Notice: Subject to any disclaimer, the term of this patent is extended or adjusted under 35 U.S.C. 154(b) by 316 days.

This patent is subject to a terminal disclaimer.

(21) Appl. No.: 12/361,664

(22) Filed: Jan. 29, 2009

(65) Prior Publication Data

US 2009/0236528 A1 Sep. 24, 2009

Related U.S. Application Data

(63) Continuation-in-part of application No. 11/677,185, filed on Feb. 21, 2007, now Pat. No. 7,502,118, and a continuation-in-part of application No. 12/331,164, filed on Dec. 9, 2008, now Pat. No. 7,974,543, and a continuation-in-part of application No. 10/699,130, filed on Sep. 22, 2003, now Pat. No. 7,327,913.

(51) Int. Cl.
*G01B 9/02* (2006.01)
*G01J 3/45* (2006.01)

(52) U.S. Cl. ...................................................... 356/451
(58) Field of Classification Search ................. 356/128, 356/432, 451, 484, 517
See application file for complete search history.

(56) References Cited

U.S. PATENT DOCUMENTS

| 5,946,130 | A  | * | 8/1999  | Rice ........................... 359/349 |
| 6,709,857 | B2 | * | 3/2004  | Bachur, Jr. ................. 435/288.7 |
| 7,277,178 | B2 | * | 10/2007 | Shpantzer et al. ............ 356/451 |
| 7,327,913 | B2 | * | 2/2008  | Shpantzer et al. ............. 385/15 |
| 7,426,035 | B2 | * | 9/2008  | Shpantzer ..................... 356/451 |
| 7,483,600 | B2 | * | 1/2009  | Achiam et al. .................. 385/14 |
| 7,502,118 | B2 | * | 3/2009  | Shpantzer ..................... 356/451 |
| 2009/0220246 | A1 | * | 9/2009 | Khurgin et al. ............... 398/141 |

* cited by examiner

*Primary Examiner* — Michael A Lyons
(74) *Attorney, Agent, or Firm* — Nadya Reingand

(57) ABSTRACT

A photo-thermal, interferometric spectroscopy system is disclosed that provides information about a chemical, such as explosives and the like, at a remote location. It may be used for solid residue detection on a surface. The system includes a novel light detector system with a matrix of optical elements focusing portions of a received light beam on input waveguides of an optical combiner. The combiner adjusts the phases of the received beam portions and combines them together to maximize the intensity of an output beam. The output beam is detected by a detector, and information about at least one of, absorption spectrum and concentration of the chemical is recovered. In the preferred embodiment the detector is a coherent detector based on 90-degrees optical hybrid.

20 Claims, 5 Drawing Sheets

(a)

(b)

(a)

(b)

CHEMICAL SENSING SYSTEM AND METHOD

CROSS-REFERENCE TO RELATED APPLICATIONS

This application is a continuation-in-part of U.S. Ser. No. 11/677,185 filed Feb. 21, 2007 now U.S. Pat. No. 7,502,118, Ser. No. 12/331,164 filed Dec. 9, 2008 now U.S. Pat. No. 7,974,543 and Ser. No. 10/669,130, now U. S. Pat. No. 7,327,913, filed Sep. 22, 2003, all of which applications are fully incorporated herein by reference.

FIELD OF INVENTION

This invention relates generally to systems and methods for chemical detection such as explosives and others, and more particularly to photothermal interferometric spectroscopy devices, and their methods of use, based on optical signal detection.

BACKGROUND OF THE INVENTION

The principles of photothermal spectroscopy are generally described in a publication by Stephen E. Bialkowski entitled "Photothermal Spectroscopy Methods for Chemical Analysis", John Wiley & Sons, Inc., 1996, the entire content of which is incorporated by reference herein. Photothermal spectroscopy method allows carrying out extremely sensitive measurements of optical absorption in homogeneous media. It is possible, using a laser's coherent and powerful output, to obtain extremely sensitive measurements of optical absorption that exceed those of mass spectroscopy by two or three times, and produce accurate results from only a few molecules.

McLean et al. (E. A. McLean et al. American Journal Applied Physics Letters, 13, p. 369 (1968)) recognized that the optical absorption resulting in sample heating and subsequent changes in refractive index would cause a phase shift in light passing through the heated region. This phase shift can be detected by interferometric means.

Grabiner et al. (F. R. Grabiner et al. Chemical Physics Letters, 17, p. 189 (1972)) proposed to use two lasers for photothermal interferometric spectroscopy: pulsed infrared laser for the medium excitation and visible probe laser for the refractive index change measurement.

In the U.S. Pat. No. 6,709,857 a system and method for monitoring the concentration of a medium using photothermal spectroscopy is disclosed. The system and method each employs an energy emitting device, such as a laser or any other suitable type of light emitting device, which is adapted to emit a first energy signal toward a location in the container. The first energy signal has a wavelength that is substantially equal to a wavelength at which the medium absorbs the first energy signal so that absorption of the first energy signal changes a refractive index of a portion of the medium. The system and method each also employs a second energy emitting device, adapted to emit a second energy signal toward the portion of the medium while the refractive index of the portion is changed by the first energy signal, and a detector, adapted to detect a portion of the second energy signal that passes through the portion of the medium. The system and method each further employs a signal analyzer, adapted to analyze the detected portion of the second energy signal to determine an amount of a sample in the container based on a concentration of the medium in the container.

There is a need for reliable remote methods and systems for detecting the presence of chemicals in the field. When the probe light illuminates a chemical located far away from the detector, the collected portion of the beam, which carries information about the chemical, has low intensity. There is a need to provide highly sensitive receivers to improve signal-to-noise ratio of the detected signal, which gives an opportunity to detect chemicals remotely.

SUMMARY OF THE INVENTION

Accordingly, an object of the present invention is to provide improved methods and systems directed to chemical detection, such as explosives and the like, at remote location. Yet another object of the present invention is to provide photothermal interferometric spectroscopy devices, and their methods of use, for the remote detection of chemicals.

These and other objects of the present invention are achieved in a system having a light detector system with a matrix of optical elements focusing portions of a received light beam on input waveguides of an optical combiner. The combiner adjusts the phases of the received beam portions and combines them together to maximize the intensity of an output beam. The output beam is detected by a detector, and information about at least one of, absorption spectrum and concentration of the chemical is recovered. In the preferred embodiment the detectors is a coherent detector with 90-degrees optical hybrid connected to at least two balanced photodetectors. The coherent detector performs homodyne detection of the light beam passed through the chemical.

The combiner is a device selected from at least one of, an integrated device, a free-space optical link device, and a fiber optics device. It comprises $2^M$ input waveguides, where M is integer $\geq 2$, receiving portions of the optical beam; $(2^M-1)$ couplers; each coupler is formed by two waveguides, coming in and out of the coupler; in each coupler one output waveguides is used in control means for changing an input phase of the optical beam portion in the same waveguide before its coupling; one output waveguide forming an input waveguide for a consequent coupler from $(2^M-1)$ couplers; an output waveguide from the last coupler forming an output beam of the device; and the control means change the input phases to maximize the output beam energy.

Yet another object of the present invention is a system for detection of chemical residue on a surface. In one embodiment the chemical may be at an explosive site, a site of pollution and a site of a chemical weapon.

Yet another object of the present invention is a system with a first light source assembly that emits a first beam, the first beam having one or more wavelengths that interact with the chemical and change a refractive index of the chemical and a second laser that produces a second beam, the second beam interacting with the chemical with changed refractive index. After passing through the chemical the beam is detected by the detector system. The detector system is positioned remote from the chemical to receive at least a portion of the beam.

In another embodiment of the present invention, a method is provided for determining information about a chemical at a remote location. The method includes receiving at least a part of a light beam passed through the chemical, compensating phase distortions in the light beam passed through the chemical by adjusting portions of the received beam using a beam combiner, detecting an output signal from the beam combiner and measuring a phase shift of the light beam being indicative of at least one of, absorption spectrum and concentration of the chemical. In particular method provides a procedure for a solid residue detection on a surface. The detection is performed using a coherent detector with 90-degrees optical hybrid.

DETAILED DESCRIPTION OF THE PREFERRED EMBODIMENT

The present invention now will be described more fully hereinafter with reference to the accompanying drawings, in which the preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

This multi-modal spectroscopy system acquires the target and remotely senses the presence of explosive residues via their unique direct light absorption (MWIR mode) and/or Raman induced absorption (LWIR mode) signatures. In operation, a tunable pulsed laser subsystem strobes the surface molecules inducing an abrupt minute change in the refractive index of the target. This in turn results in a phase change in the returned probe laser beam that is measured by the co-located analyzer receiving system. The analyzer consists of novel digital coherent pulsed interferometer that is capable of extracting the signal-derived phase change from air-turbulence, target movement and vibration.

The system and method of the present invention provide a tool for standoff detection of vapor chemicals and chemical residues on a surface with a special interest to the explosives detection.

Figure 1:
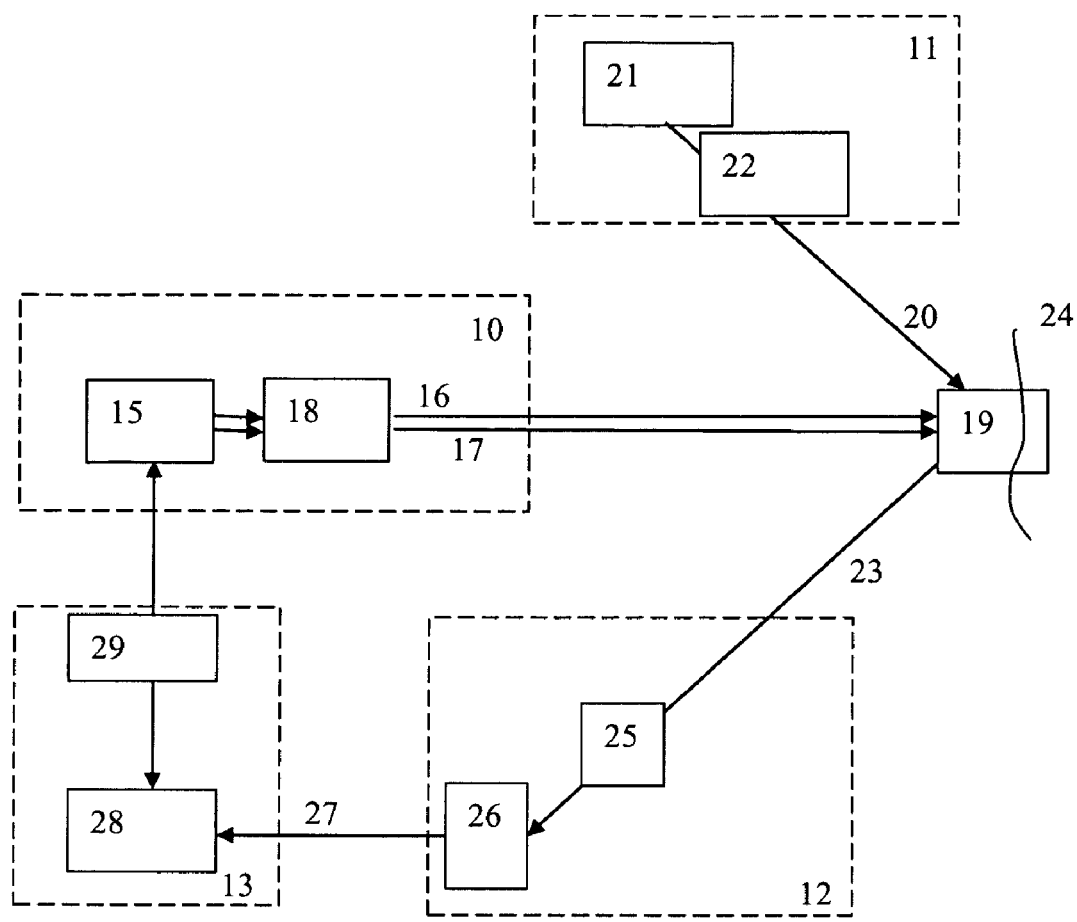
FIG. 1 is a block diagram of a photothermal interferometric spectroscopy system of the present invention that has a temporal referenced beam: (a) with reflected probe beam, (b) with transmitted probe beam.
Figure 1:
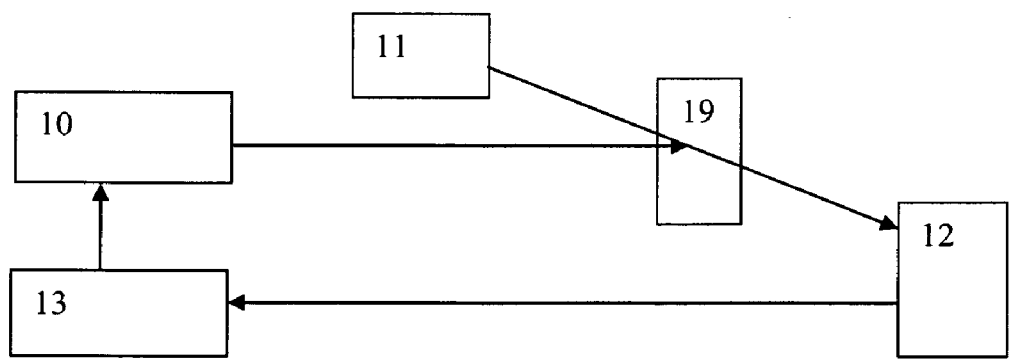

In one embodiment of the present invention, an optical device is provided, the block diagram of which is shown in FIG. 1(a), where 10 is a unit that combines strobe generation and targeting, 11 is the unit for optical probe beam generation and targeting, 12 is a signal detection and recovery block, and 13 is electronics control and processing block.

The proposed spectroscopy in the LWIR exploits the information rich 6-8 μm wavelength range resulting in enhanced sensitivity and selectivity towards nitrogen-containing explosives. In general, Raman features in the 6-8 μm region are highly specific and unique. Likewise, the important class of peroxide-based explosives also has features nearby that are accessible. The excitation of explosives residues in the LWIR is accomplished non-parametrically via a 4-wave mixing process known as "stimulated" Raman. This is implemented by spatially and temporally overlapping two transmitted near IR photons, produced by an Optical Parametric Oscillator (OPO) strobe laser, at the surface residue target 24. Specifically, the strobe laser OPO 15 produces both a pump signal 16 (Pump @ 1.808-1.878 μm) and idler 17 (Stokes @ 2.588-2.455 μm) beams that are eye-safe and suffer negligible attenuation in the atmosphere at ranges up to and beyond the 30 m requirements. The beams 16 and 17 are directed to the target by a targeting unit 18. Stimulated Raman (SR) offers the number of advantages over the direct MWIR absorption approach for identifying explosives surface residues.

In the preferred embodiment the strobe beam wavelengths can be tuned between wavelengths in 1 ms or less.

The entire Raman-active vibrational manifold between 6-8 μm of explosive species can be acquired in air and over long paths; lasers exploit the most information-rich spectral regions. The OPO laser output can be controlled and directed at specific characteristic resonances; fewer lines required for definitive identification enables more rapid surface surveillance. Theoretical models support the notion that the energy deposited in the target via a SR process rivals that of direct absorption: good signal strength suitable for PTI detection. SR is more selective, minimizing potential interferent background complications (reduced spectroscopic clutter), thereby simplifying the chemometrics problem, leading to improved detection probability. The SR approach allows co-propagation of strobe (signal and idler) and probe beams, simplifying the system concept.

The strobe laser source supporting the direct absorption approach to explosives detection is a frequency agile MWIR laser transmitter using an efficient single longitudinal mode 1064 nm Nd:YAG oscillator to pump a line-narrowed, dual crystal PPLN OPO to generate MWIR pulses at a repetition rate of 1 kHz that are tunable between 3.1 and 3.6 μm at rates up to 1 kHz. The fast tuning rate allows the interrogation time to stay within 90 seconds or less. Chemometric algorithms necessary for optimizing the selection of the laser lines for the detection of explosives residues on selected surfaces, cognizant of atmospheric propagation and prospective interferents limitations, are used in concert with PTI data processing algorithms to extract explosives' identities.

The chemical under study is also illuminated by a probe beam (this beam is called "the second beam") or a set of beams 20 coming from the light source 21 and passing the targeting unit 22. In the preferred embodiment of the present invention, shown in FIG. 1(a), the probe set of beams 23 passed the interrogated chemical is reflected by the reflection surface 24. A collecting unit 25 collects the part of reflected light (this beam is called "the third beam") and forwards it to coherent detector 26 that includes 90-degrees optical hybrid. The collecting unit 25 will be described in more details in the following paragraphs. The electrical output signal 27 from the coherent detector is processed in DSP unit 13. Digital synthesizer and control unit 29 controls DSP signal processor 28, optical parametric oscillator 15.

The disclosed PTI method is applicable to detect both trace vapors and chemical residues on solid surfaces. In case of vapors, the examined chemical volume 19 is right in front of the reflecting surface 24. In case of chemical residues, both the strobe and the probe lasers are focused on the interrogated surface 24.

Another embodiment of the present invention is a system operating without the background reflection surface. The background surface can be eliminated if there is enough back scattered light in the interrogated chemical volume to carry out the detection.

FIG. 1(b) shows another embodiment of the present invention. This is the analogous scheme for the chemicals detection, but operating in the transmission mode. In certain situations it could be possible to install the light transmitter 11 and detector 12 on the opposite sides of the interrogated chemical volume 19. This allows the chemical detecting without background reflection surface.

The detected molecules can be brought into the excited state from which it relaxed by the following processes: (i) direct one-photon absorption; (ii) two-photons absorption and (iii) two-photons stimulated Raman process. The stimulated Raman process enables the use of less exotic light sources that simplify and optimize the overall system.

Probing of the interrogated chemical is performed by one of two methods: (1) Temporal referenced method, (2) Spatial referenced method, both of which are described in more details in U.S. patent application Ser. No. 11/677,185 filed Feb. 21, 2007 by the same team of inventors. In temporal method, the probe pulse is split into two pulses: one before strobe pulse and another—after the strobe pulse. In spatial referenced method, the probe beam comprises two beams distant in space, each having a pulse. The first beam pulse passes aside of the interrogated volume, while the second beam pulse goes through it. In both cases, the second pulse carries information about the interrogated medium reaction on the strobe beam, which is encoded in its phase change. This information is decoded using a coherent optical receiver, where the first pulse and the second pulse interfere. The coherent receiver is followed by a digital signal processing to obtain the data on the chemical concentration or absorption spectrum. The calculations below show that the minimum detectible concentration is $10^{-10}$ cm$^{-1}$ that is better than 1 ppb. Further reduction of the minimum detectable concentration can be achieved by increasing the light collection efficiency 7, since the concentration is proportional to $\gamma^{-1/2}$.

U.S. patent application Ser. No. 11/677,185 from the same assignee discloses light collection from a relatively large area with the use of phase distortion correction by adaptive optics and implementation of multimode fibers with multimode-to-single-mode coupler. This patent application is fully incorporated herein by reference. In the present patent application we address the same problem, but propose the use of an integrated device, so called optical combiner, to adjust phase distortions of received light over a relatively large area. This optical beam combiner was described in details in U.S. patent application Ser. No. 12/331,164 filed Dec. 9, 2008 from the same assignee; it is fully incorporated herein by reference.

Figure 2:
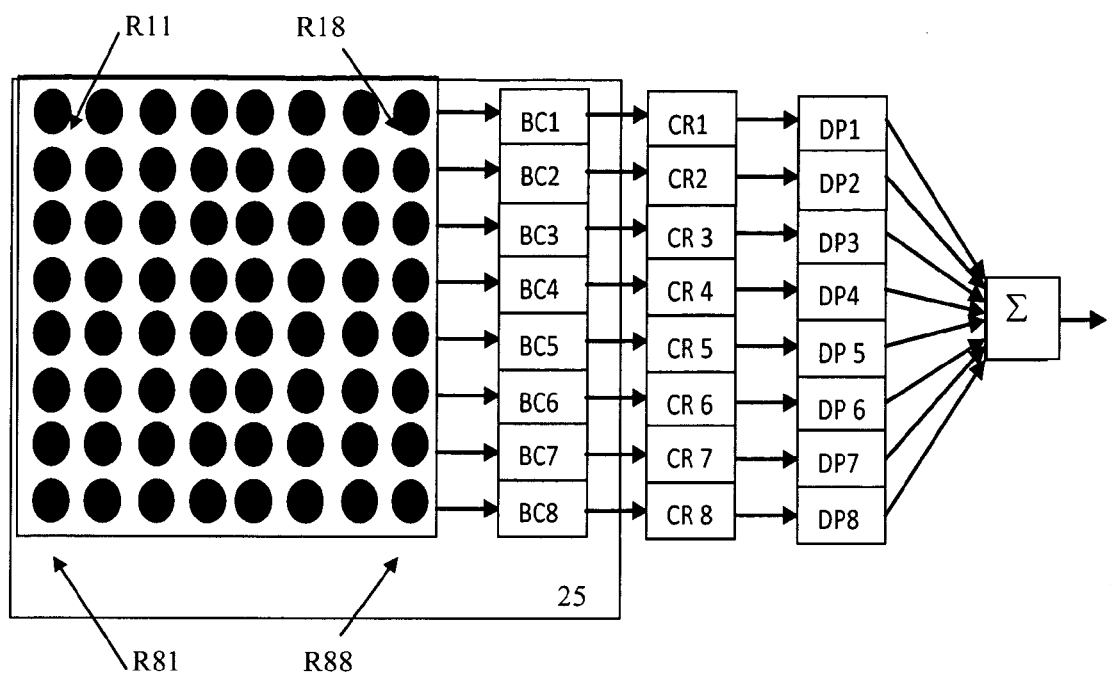
FIG. 2 is a block diagram of a large area receiver according to the present invention.

FIG. 2 shows the large area receiver, which includes a matrix of N×N optical elements (where N is any integer number) to focus the receiving beam portions. In FIG.2 N is equal to 8 as an example. For example, the optical elements may be a set of microlenses. The receiver further includes a set of beam combiners BC1-BC8, followed by a set of coherent detectors CD1-CD8 with digital signal processors DP1-DP8. The output signals from the processors are mixed together in a unit Σ. The optical elements matrix and the set of beam combiners form the collecting unit 25 of FIG. 1(a).

Figure 3:
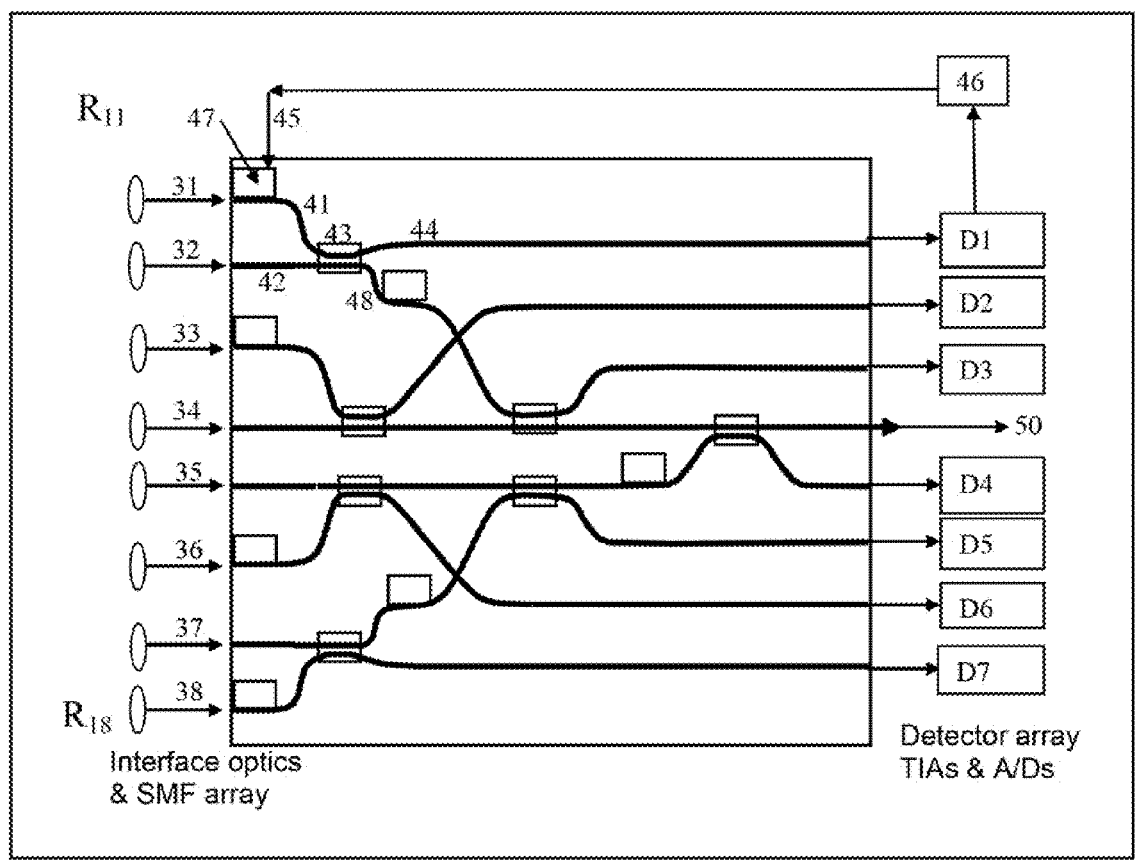
FIG. 3 is a schematic diagram of an optical combiner to collect the light from multiple apertures.

The light, received by a row of lenses, is inserted into waveguides of the combiner. For example, the light from lenses R11-R 18 is inserted in input waveguides of the combiner BC1 as shown in FIG. 2. FIG. 3 provides more details on the combiner structure. Each combiner has (M−1) stages of directional couplers with two output branches each, where one output branch serves for control. The operation of each stage is the following. The waveguides 41 and 42 are coupled together by a coupler 43. The signal from the output 44 is detected by a first detector D1. The signal power detected by the detector D1 is minimized by detecting the signal and applying a correction signal 45 via electronic unit 46 to the phase modulator 47 that changes the phase of the signal in the input waveguide 41 until it is shifted by exactly 90 degrees from the signal in the waveguide 42. When the phase shift is equal to 90 degrees, a constructive interference occurs in the output branch 48 and a destructive in 44. When the signal in the branch 44 is equal to zero, it does not control the phase modulator any longer. In similar manner, the combiner mixes each pair of waveguides and maximizes the output beam from the waveguide 50. In another embodiment the electronic unit 46 controls not only the modulator 47 but also the coupling ratio of the coupler 43 thus maximizing the light beam in the waveguide 48. This is disclosed in more details in U.S. patent application Ser. No. 12/331,164 filed Dec. 9, 2008.

Figure 4:
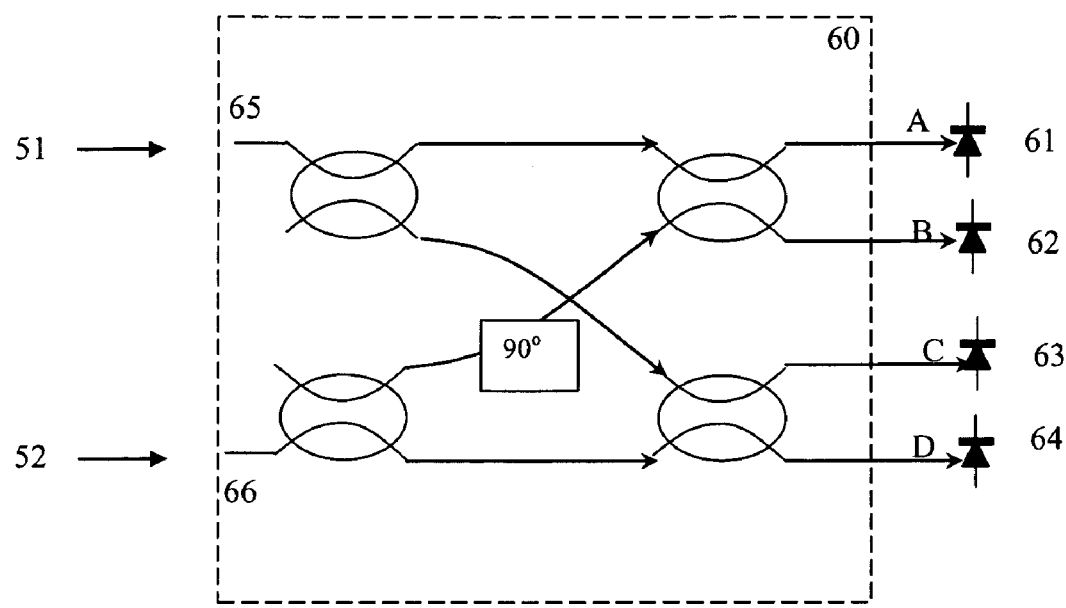
FIG. 4 is a schematic diagram of a balanced detector of the present invention with 90-degrees optical hybrid.

The output signal 50 serves for the further processing, for example, for recovery of the information encoded in the beam. The phase delay in the probe beam is measured by interfering the probe signal with its time delay (or space separated) version using coherent detectors. The schematic diagram of the coherent detector is shown in FIG. 4. In one embodiment, it consists of a 90-degrees optical hybrid 60 and four balanced photodetectors 61-64. Two incoming optical signals 51 and 52, called, respectively, the signal S and the local oscillator L, impinge two inputs 65 and 66 of the optical hybrid. Both signal beam S and local oscillator L beam are divided by the first set of 3 dB couplers and mixed together with an additional phase shift of 90 degrees. The resulting four output signals A, B, C, D, all have 90 degrees relative phase difference of the form: A=S+L, B=S−L, C=S+jL and D=S−jL.

In the preferred embodiment the balanced detector is used as described in the U.S. patent application Ser. No. 10/669,130 "Optical coherent detector and optical communications system and method" by I. Shpantzer et al. incorporated herein by reference.

Figure 5:
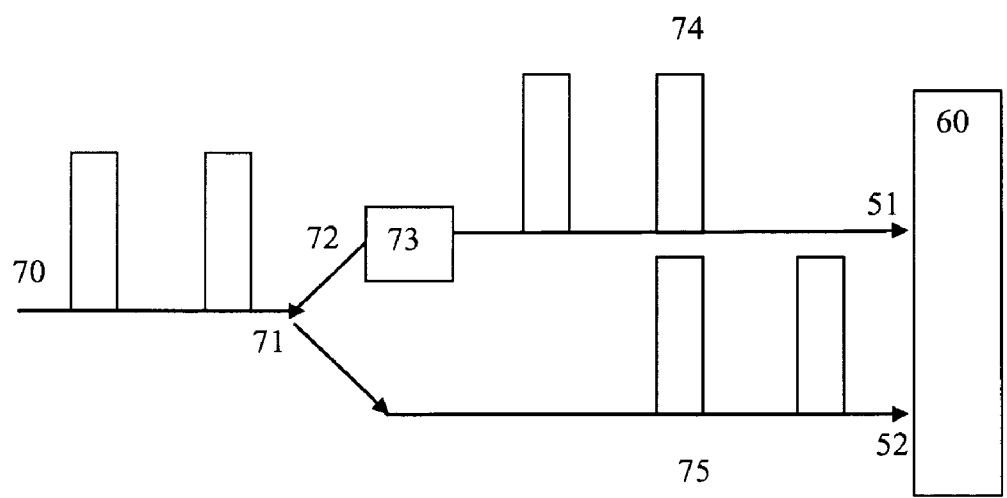
FIG. 5 illustrates formation of two beams, one of them being delayed from another.

FIG. 5 shows the overlapping of the time delayed signal at the detector. Incoming signal 50 is splitted at splitter 71, and the beam 72 experiences the delay at the delay line 73. The delay time is chosen to be the same as a time delay between two pulses in the pair. As the result of this delaying of one of the beams, the pulses 74 and 75 impinge the optical hybrid 60 at the same time. Since the pulse 74 corresponds to the heated chemical, and pulse 75 is the reference pulse, the information of the phase change in the laser beam due to the refractive index change can be recovered after detection. These two beams form input beams 51 and 52 for the coherent detector 60 of FIG. 4.

In the preferred embodiment 10 mJ pulses at required decent repetition rate are obtained using regenerative amplifiers produced by Positive Light, Santa Clara, Calif.

EXAMPLE 1

Chemical Residues Detection on Solid Surfaces

Figure 6:
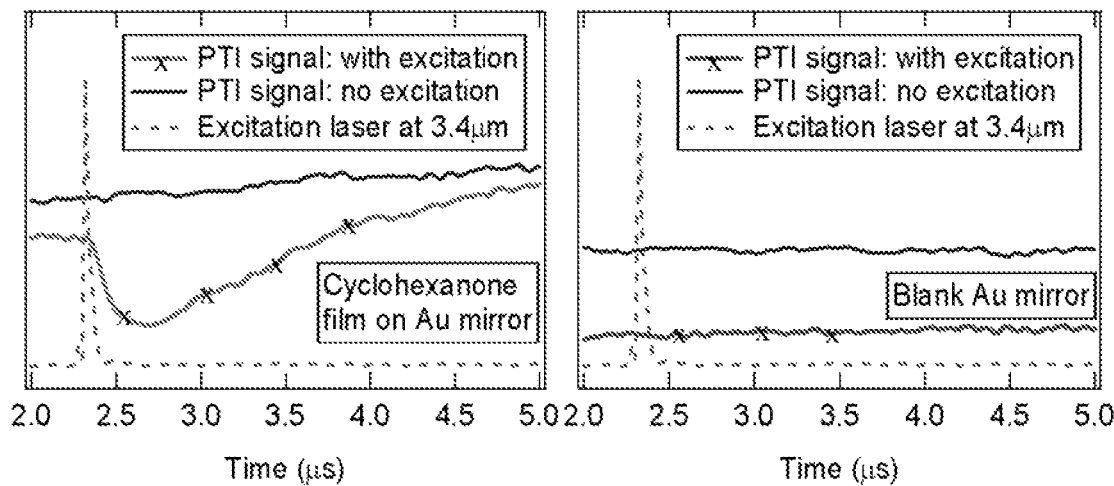
FIG. 6 shows experimental study of Cyclohexanone film on Au mirror surface: waveforms of PTI signals with and without excitation laser pulse.
Figure 7:
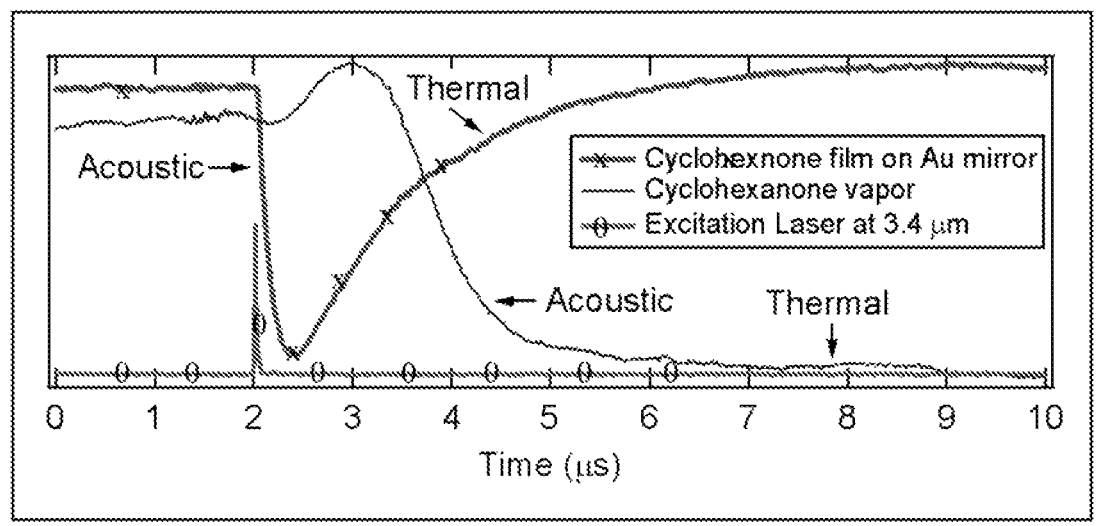
FIG. 7 illustrates the high-resolution PTI phase shift for non-vapor-phase and vapor phase Cyclohexanone.

To address the question of whether PTI will be successful for condensed phase measurements as it is for gas phase, a single MWIR laser frequency at 3.4 μm was used to strobe a thin film of cyclohexanone deposited on a gold mirror. The gold mirror in this instance merely provides a suitably reflective, but otherwise spectroscopically innocent, substrate. The objectives of this experiment were to verify the existence of a measureable photothermal effect and then to compare the dynamics of the relaxation transient from a condensed phase source to that derived from a vapor phase source. Oscilloscope waveforms of real-time PTI signals obtained from the cyclohexanone-coated gold mirror with and without strobe laser excitation are shown in FIG. 6. Of particular significance is the presence of a prominent (signal-to-background ratio of the fast acoustic transient is better than 20 dB) and rapid PTI acoustic transient directly correlated to the exciting laser pulse which is unambiguous evidence of cyclohexanone absorption. By contrast, no such transient was observed with a clean blank gold mirror. The comparison between the PTI waveforms for vapor-phase cyclohexanone versus the cyclohexanone film is shown in FIG. 7. Note that the PTI acoustic transient of the film exhibits both a more rapid onset and faster decay to the long-time thermal recovery component than those of the vapor. The underlying MWIR absorption driven density perturbations that lead to phase changes in the probe laser are not only observed in an optically thin condensed phase, but are associated with faster dynamics leading to enhanced measurements sensitivity. PTI is applicable to the interrogation of condensed phases on surfaces.

The description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A photo-thermal interferometric spectroscopy system that provides information about a chemical at a remote location, comprising: a light detector system positioned remotely from the chemical, the detector system having a matrix of optical elements focusing portions of a received light beam on input waveguides of an optical combiner; the combiner adjusting the phases of the received beam portions and combining them together, wherein the phases of the beam portions are adjusted to maximize the intensity of an output beam; a detector detecting the output beam; and a digital signal processing unit, connected to the detector, recovering information about at least one of absorption spectrum and concentration of the chemical.

2. The system of claim 1, further comprising: a first light source assembly that emits a first beam, the first beam having one or more wavelengths that interact with the chemical and change a refractive index of the chemical; a second laser that produces a second beam, the second beam interacting with the chemical with changed refractive index forming a third beam; the third beam forming the received light beam.

3. The system of claim 2, wherein the first light source beam generates a spectrum of wavelengths in at least one of the near, mid and far infrared ranges.

4. The system of claim 3, wherein the first light source wavelengths are tunable.

5. The system of claim 2, wherein the first light source beam consists of two beams with two different wavelengths that results in stimulated Raman absorption in the chemical.

6. The system of claim 5, wherein the Raman absorption is in 6-8 micron range.

7. The optical system of claim 2, wherein the second laser is a pulsed light source.

8. The system of claim 1, wherein: the detector includes a coherent receiver having a 90-degree optical hybrid connected to at least two balanced photodetectors.

9. The optical system of claim 8, wherein the detector system provides homodyne detection of the light beam passed through the chemical.

10. The system of claim 1, wherein the chemical is in the form of a gas, liquid or solid.

11. The system of claim 1, wherein the chemical is a solid residue on a surface.

12. The system of claim 1, wherein the chemical is at an explosive site, a site of pollution or a site of a chemical weapon.

13. The system of claim 1, wherein the optical combiner comprises: $2^M$ input waveguides, where M is an integer $\geq 2$, receiving portions of the optical beam; $(2^M-1)$ couplers; each coupler formed by two waveguides, coming in and out of the coupler; in each coupler one output waveguide is used in control means for changing an input phase of the optical beam portion, which enters the same coupler; one output waveguide forming an input waveguide for a consequent coupler from $(2^M-1)$ couplers; an output waveguide from the last coupler forming an output beam of the device; and wherein the control means changes the input phases to maximize the output beam energy.

14. The optical system of claim 13, wherein the combiner is a device selected from at least one of, an integrated device, a free-space optical link device, and a fiber optics device.

15. The optical system of claim 1, wherein the remote location is selected from, a standoff location, outside of a blast range, inside a blast range, and at an entry point.

16. A method for determining information about a chemical at a remote location, comprising: receiving at least a part of a light beam passed through the chemical; compensating phase distortions in the light beam passed through the chemical by adjusting portions of the received beam using a beam combiner; detecting an output signal from the beam combiner, and measuring a phase shift of the light beam being indicative of at least one of absorption spectrum and concentration of the chemical.

17. The method of the claim 16, wherein the chemical is a solid residue on a surface.

18. The method of the claim 16, further comprising: illuminating the chemical with a strobe beam having two beams with different wavelengths resulting in stimulated Raman absorption in the chemical; illuminating the chemical with a probe beam, and the probe beam passing through the chemical.

19. The method of the claim 16, further comprising: detecting an output signal from the beam combiner using a coherent detector with a 90-degree optical hybrid; the detector connected to a digital signal processing unit, which provides information about the phase shift of the light beam indicative of at least one of absorption spectrum and concentration of the chemical.

20. The method of the claim 16, wherein the optical combiner comprises: $2^M$ input waveguides, where M is an integer $\geq 2$, receiving portions of the optical beam; $(2^M-1)$ couplers; each coupler formed by two waveguides, coming in and out of the coupler; in each coupler one output waveguide is used in control means for changing an input phase of the optical beam portion, which enters the same coupler; one output waveguide forming an input waveguide for a consequent coupler from $(2^M-1)$ couplers; an output waveguide from the last coupler forming an output beam of the device; and wherein the control means changes the input phases to maximize the output beam energy.

* * * * *